(12) United States Patent
Grossi et al.

(10) Patent No.: US 8,742,077 B2
(45) Date of Patent: Jun. 3, 2014

(54) METHOD FOR PREPARING
1,6:2,3-DIANHYDRO-β-D-MANNOPYRANOSE

(75) Inventors: Pierre Jean Grossi, Paris (FR);
Christian Hoff, Paris (FR);
Jean-Claude Rovera, Paris (FR);
Raphael Sole, Paris (FR)

(73) Assignee: Sanofi, Paris (FR)

( * ) Notice: Subject to any disclaimer, the term of this patent is extended or adjusted under 35 U.S.C. 154(b) by 403 days.

(21) Appl. No.: 13/119,326

(22) PCT Filed: Sep. 15, 2009

(86) PCT No.: PCT/FR2009/051729
§ 371 (c)(1),
(2), (4) Date: May 9, 2011

(87) PCT Pub. No.: WO2010/031953
PCT Pub. Date: Mar. 25, 2010

(65) Prior Publication Data
US 2011/0213141 A1    Sep. 1, 2011

(30) Foreign Application Priority Data
Sep. 16, 2008  (FR) ..................... 08 05062

(51) Int. Cl.
*C07H 3/02* (2006.01)
(52) U.S. Cl.
CPC ...................................... *C07H 3/02* (2013.01)
USPC ...................................................... 536/1.11
(58) Field of Classification Search
None
See application file for complete search history.

(56) References Cited
PUBLICATIONS

Hatanaka et al., Polymer Journal, 2000, 32, 974-976.*
Hardegger et al., "Ditosylation of Glucose" Helvetica Chimica Acta (1948) vol. 31 pp. 1863-1867.*
Bailliez, V. et al., "A Practical Large-Scale Access to 1,6-Anhydro-β-$_D$-hexopyranoses by a Solid-Supported Solvent-Free Microwave-Assisted Procedure," Synthesis (2003), vol. 7, pp. 1015-1017.
Wolfgang Holla, E. et al., "Two Syntheses of 3-Azido-3-deoxy-$_D$-mannose," Synlett (1992), pp. 413-414.
Akagi, Masuo et al., "A New Synthesis of 1,6-Anhydro-β-$_D$-glucopyranose (Levoglucosan)," Pharmaceutical Society of Japan (1962), vol. 10, pp. 905-909.
Miljkovic, Dusan et al., "A convenient route to 6-functionalized derivatives of $_D$-glucal," Carbohydrate Research (1989), vol. 193, pp. 275-278.
International Search Report dated Jan. 22, 2010.

* cited by examiner

*Primary Examiner* — Eric S Olson
(74) *Attorney, Agent, or Firm* — Scully, Scott, Murphy & Presser, P.C.

(57) ABSTRACT

The invention relates to a method for preparing 1,6:2,3-dianhydro-â-D-mannopyranose and is characterized in that it includes a step of cyclizing the compound C, where R is an alykyl group and R' is an activating agent, in an alcohol/alcoholate mixture under anhydrous conditions.

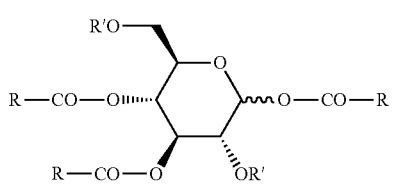

13 Claims, No Drawings

METHOD FOR PREPARING 1,6:2,3-DIANHYDRO-β-D-MANNOPYRANOSE

The present invention relates to a novel process for the preparation of 1,6:2,3-dianhydro-β-D-mannopyranose, denoted hereinafter as "Cerny epoxide" or "compound (I)", corresponding to the following formula, in which the bold lines represent bonds situated above the pyranose ring:

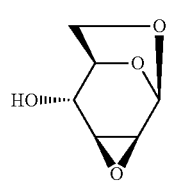
(I)

or, according to another representation:

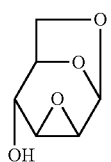
(I)

Compound (I) and more generally the compounds of the family of the 1,6: (2,3 and 3,4)-dianhydro-β-D-hexopyranoses have essentially been described a Czech chemist, Miloslav Cerny. Three access routes to the Cerny epoxide (I) from compound 1 (1,6:3,4-dianhydro-2-O-tosyl-β-D-galactopyranose) are found in the literature:

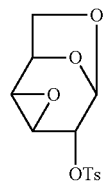
1

The compound 1 is obtained from levoglucosan 2 (or 1,6-anhydro-β-D-glucopyranose), as represented below (M. Cerny et al., Collect. Czech. Chem. Commun., 1961, vol. 26, pp. 2542-2550):

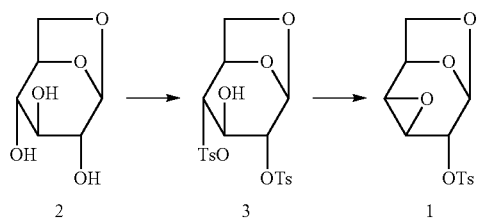 [SMILES: OC1C2COC(O2)C(O)C1O ; Cc1ccc(S(=O)(=O)OC2C3COC(O3)C(OS(=O)(=O)c3ccc(C)cc3)C2O)cc1 ; Cc1ccc(S(=O)(=O)OC2C3OCC(O3)C3OC32)cc1]

The ditosylated derivative 3 (1,6-anhydro-2,4-di-O-tosyl-β-D-glucopyranose) is selectively obtained (80%). The remaining 20% are essentially composed of the tritosylated derivative. The overall yield for the conversion of compound 2 to compound 1 is 55%.

There are many access routes to levoglucosan 2; those most used industrially are, in addition to the pyrolysis of starch and cellulose described since the 1960s, the cyclisations in a basic or acidic medium of D-glucose represented below:

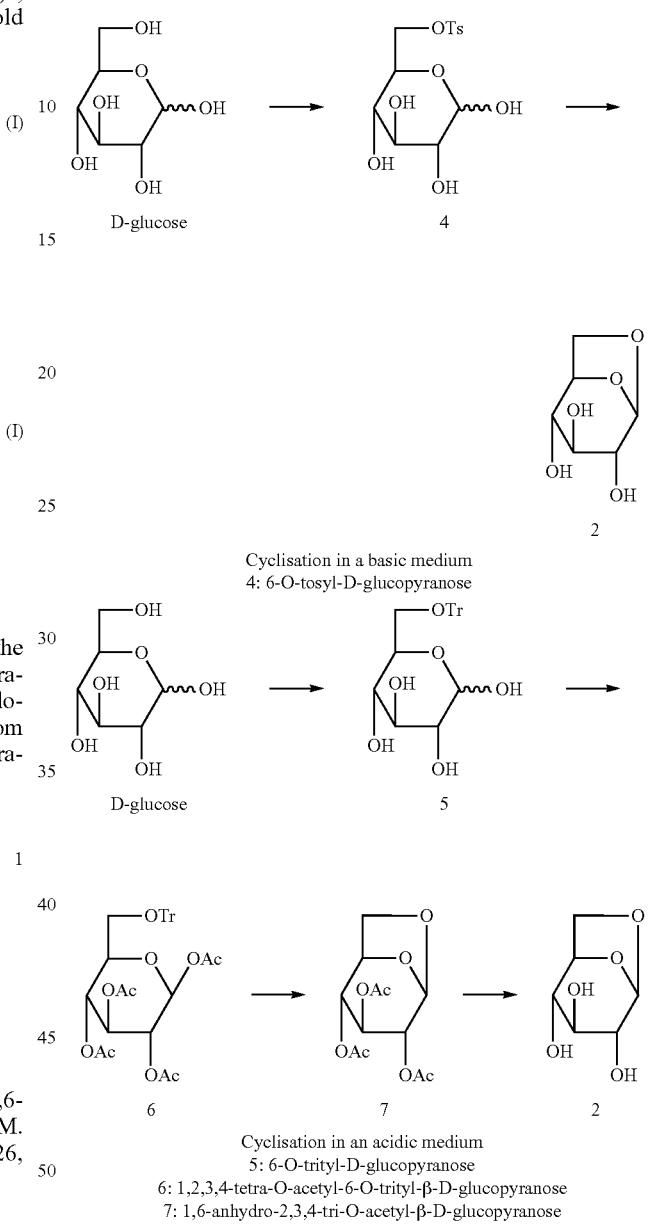

Cyclisation in a basic medium
4: 6-O-tosyl-D-glucopyranose

Cyclisation in an acidic medium
5: 6-O-trityl-D-glucopyranose
6: 1,2,3,4-tetra-O-acetyl-6-O-trityl-β-D-glucopyranose
7: 1,6-anhydro-2,3,4-tri-O-acetyl-β-D-glucopyranose The cyclisation in a basic medium (M. A. Zottola et al., J. Org. Chem., 1989, vol. 54, pp. 6123-6125; M. Akagi et al., Chem. Pharm. Bull., 1962, vol. 10, pp. 905-909) is reflected by a low yield (15%). Furthermore, it is necessary to acetylate the crude levoglucosan 2 in order to allow it to be isolated. With regard to the route of cyclisation in an acidic medium (M. V. Rao et al., Carbohydrate Research, 1987, vol. 162, 141-144; R. L. Wistler et al., Methods Carbohydr. Chem., 1972, vol. 6, pp. 411-412; E. Zara-Kaczian et al., 1982, vol. 111, No. 3, pp. 271-283; E. Zara-Kaczian et al., Acta Chemica Acad. Scient. Hung., 1978, vol. 96, No. 3, pp. 311-313), it is described with a better yield (70%) but it comprises a further two stages.

The three access routes to the Cerny epoxide (I) from compound 1 are as follows.

Route 1:

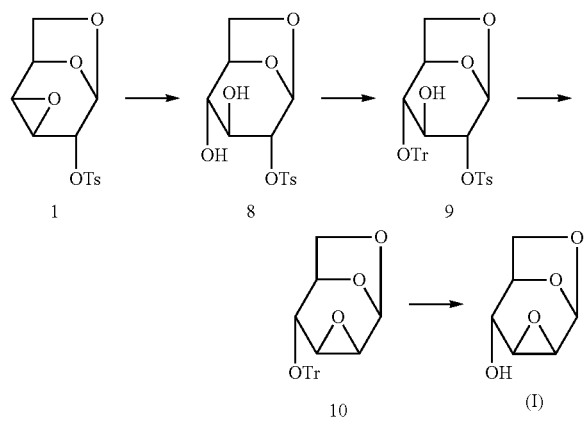

8: 1,6-anhydro-2-O-tosyl-β-D-glucopyranose
9: 1,6-anhydro-2-O-tosyl-4-O-trityl-β-D-glucopyranose
10: 1,6:2,3-dianhydro-4-O-trityl-β-D-glucopyranose In addition to the number of stages necessary to arrive at the Cerny epoxide (I), this sequence comprises, inter alia, the difficulty of selectively hydrolysing the 3,4-anhydro functional group during the first stage. The hydroxyl in the 4 position of the monotosylated derivative 8 is subsequently protected by a trityl group (Tr) in order to prevent the epoxide from migrating during the cyclisation in the presence of sodium ethoxide (EtONa).

Route 2:

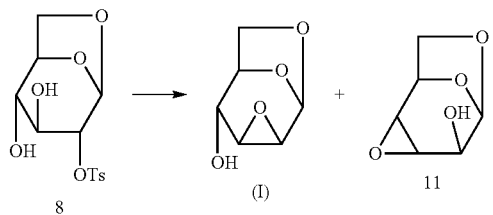

According to M. Cerny et al. (Synthesis, 1972, 698-699), the Cerny epoxide (I) can be obtained from the derivative 8 in the presence of Amberlite IRA 400/OH⁻ resin. However, prolonged contact with the resin results in the migration of the epoxide into the 3,4 position and the formation of the derivative 11 (1,6:3,4-dianhydro-β-D-altropyranose). The difficulty in selectively obtaining the compound (I) thus remains. The starting compound 8 is itself also difficult to selectively obtain, as mentioned above.

Route 3:

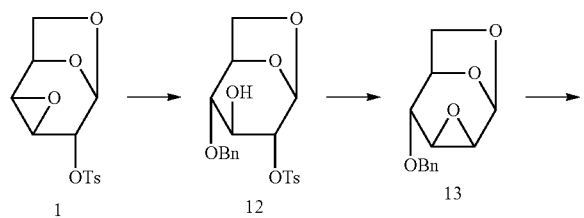

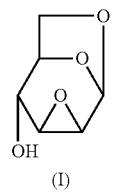

12: 1,6-anhydro-4-O-benzyl-2-O-tosyl-β-D-glucopyanose
13: 1,6:2,3-dianhydro-4-O-benzyl-β-D-mannopyranose This variant makes it possible to cyclise to give the dianhydro derivative 13 without migration of epoxide (T. Trnka et al., Collect. Czech. Chem. Commun., 1971, vol. 36, pp. 2216-2225; M. Cerny et al., Collect. Czech. Chem. Commun., 1968, vol. 33, pp. 1143-1156). Nevertheless, it comprises a large number of stages to provide the Cerny epoxide (I) from D-glucose.

In conclusion, the three access routes described above for the preparation of the Cerny epoxide (I) have respectively 10, 8 and 9 stages starting from D-glucose (using, in order to obtain levoglucosan 2, the cyclisation in an acidic medium, which is the route described with the better yield) and have, for overall yield, 0.5%, 10% and 13% respectively for routes 1, 2 and 3.

Furthermore, V. Bailliez et al. have described, in Synthesis, 2003, No. 7, 1015-1017, an access route to 1,6:3,4-dianhydro-β-D-altropyranose which is accompanied by formation of a minor amount of 1,6:2,3-dianhydro-β-D-mannopyranose as byproduct. According to these authors, the Cerny epoxide can be formed from a precursor cyclised beforehand between the 1 and 6 positions or else an N-1 precursor of Cerny epoxide acetylated in the 4 position can be obtained, at a level of 5%, in several stages from 1,3,4-tri-O-acetyl-2,6-di-O-tosyl-glucose subjected to alumina, irradiation under microwaves and per-O-acetylation.

E. W. Holla et al. have also described, in Synlett., 1992, 413-414, the use of a precursor cyclised beforehand between the 1 and 6 positions in subsequently forming the Cerny epoxide by reaction with sodium methoxide, the said epoxide being obtained as a mixture with 1,6:3,4-dianhydro-β-D-altropyranose.

In view of the costs of labour and starting materials, and in order to obtain the compound (I) on the industrial scale, it is necessary to envisage a shorter synthesis which offers a better yield and is thus more profitable. The inventors have now found an access route to the compound (I) in three stages starting from D-glucose which meets the abovementioned requirements.

The process according to the invention comprises the stages represented below in Scheme 1.

Scheme 1:

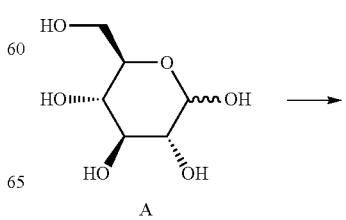

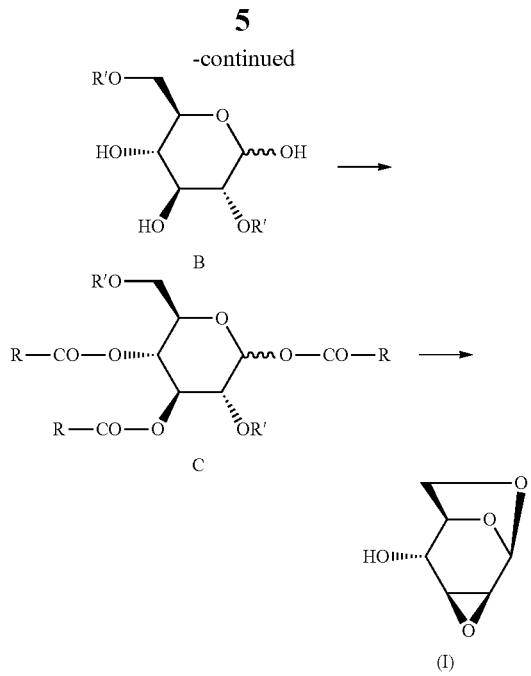

A subject-matter of the invention is thus a process for the preparation of compound (I), characterized in that it comprises a stage of cyclisation of compound C in an alcohol/alkoxide mixture under anhydrous conditions.

In compound C, R represents an alkyl group comprising from 1 to 4 carbon atoms, for example a methyl group, and R' represents an activating agent, for example a tosyl, mesyl or benzenesulphonyl group.

Within the meaning of the present invention and unless otherwise mentioned in the text:
- "alkyl" is understood to mean a saturated and linear or branched aliphatic group, for example a methyl group;
- "alcohol" is understood to mean a compound of alkyl-OH formula, in which the alkyl group is as defined above and comprises from 1 to 3 carbon atoms, for example methanol;
- "alkoxide" is understood to mean the conjugated base of the alcohol as defined above, that is to say the anion corresponding to the formula alkyl-O⁻, carrying an alkali metal counter iron, such as sodium;
- "alcohol/alkoxide mixture" is understood to mean a mixture of an alcohol with the corresponding alkoxide, for example a methanol/sodium methoxide ($CH_3OH$/$CH_3ONa$) mixture;
- "activating agent" is understood to mean an agent which makes possible the departure of the leaving group —OR' and which promotes the cyclisation reaction between the 1 and 6 positions of compound C, for example a tosyl, mesyl, benzenesulphonyl or benzenesulphonyl derivative group, such as a p-halobenzenesulphonyl halide.

According to the invention, the cyclisation of compound C is advantageously carried out using from 2 to 3 equivalents of alkoxide (expressed with respect to the molar amount of compound C), preferably 2.2 equivalents.

Another subject-matter of the invention is a process for the preparation of compound (I), characterized in that it comprises a stage of acylation of compound B (in which R' is as defined above), making it possible to obtain compound C, followed by a stage of cyclisation, as defined above, of compound C in an alcohol/alkoxide mixture.

The stage of acylation of compound B is carried out using an acylating agent which makes it possible to introduce R—CO— groups into compound C. Such an acylating agent can, for example, consist of an acid anhydride, such as acetic anhydride, or of an acyl chloride. Use is advantageously made of at least three equivalents of acylating agent with respect to compound B.

According to one embodiment of the invention, compound C is such that R represents a methyl group. In this case, the acylation reaction on compound B consists of an acetylation reaction, for example carried out using acetic anhydride, in a solvent, such as dichloromethane.

Another subject-matter of the invention is a process for the preparation of compound (I), characterized in that it comprises a stage of activation of compound A (D-glucose), which makes it possible to obtain compound B, then a stage of acylation of compound B, followed by a stage of cyclisation of compound C, obtained on conclusion of the preceding stage, in an alcohol/alkoxide mixture under anhydrous conditions.

The stage of activation of compound A can be carried out using an activating agent as defined above. Use is thus advantageously made of tosyl chloride in a solvent, such as pyridine.

The process according to the invention makes it possible to selectively obtain compound (I) (1,6:2,3-dianhydro-β-D-mannopyranose) in three stages starting from D-glucose, in particular because of the low basicity of the medium during the reaction for the cyclisation of the intermediate C, the anhydrous reaction conditions and the number of equivalents of sodium methoxide used.

Compound (I) is obtained, according to the process of the invention, with a selectivity of at least 90% from intermediate C. The chemical yield calculated with regard to the isolated product, that is to say after the various stages of washing, filtering and removing solvent required for its isolation, such as is conventional to employ in organic chemistry, is at least 60%.

The reactions for the conversion of D-glucose to intermediate B and then for the formation of the intermediate C from compound B exhibit a chemical yield of at least 50% and 80% respectively.

The invention is illustrated using the following examples, which describe in detail a process for the preparation of compound (I) in accordance with the invention, according to the following Scheme 2. In these examples, the following abbreviations are used: Me: methyl; Et: ethyl; Ac: acetyl; TLC: Thin Layer Chromatography; HPLC: High Performance Liquid Chromatography; DMAP: 4-dimethylaminopyridine.

Scheme 2:

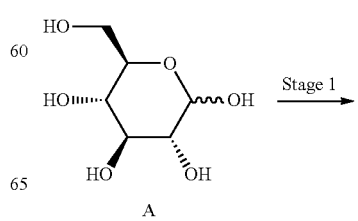

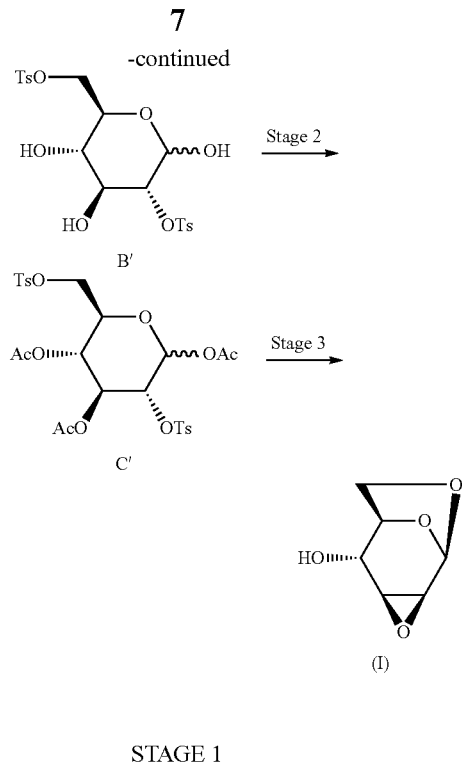

STAGE 1

Preparation of Compound B' (2,6-di-O-tosyl-glucopyranose)

250 g (1.38 mol) of D-glucose (compound A) and 1240 ml of anhydrous pyridine are successively introduced into a 6 liter reactor under nitrogen. The mixture is cooled to −10° C. with stirring. At the same time, in a second reactor, a solution of tosyl chloride in pyridine is prepared by dissolving 529 g (2.78 mol) of tosyl chloride in 1760 ml of anhydrous pyridine. The tosyl chloride solution is subsequently run onto the glucose solution prepared above. The mixture is kept stirred at −10° C. for 17 h. The degree of progression of the reaction is monitored by TLC (eluant $CH_2Cl_2$/MeOH 9/1 V/V for the quantification of the di- and tritosylated derivatives; eluant $CHCl_3$/EtOH/AcOH/$H_2O$ 48/40/8/4 V/V for the monitoring of the D-glucose) and by HPLC, under standard conditions.

The mixtures are concentrated by distillation under vacuum at 45-50° C. When the medium thickens and when the residual volume is approximately 1000 ml, 750 ml of demineralized water are charged, the mixture is homogenized and approximately 750 ml of the mixture are subsequently distilled off at a temperature of approximately 45-50° C. under approximately 20 mmHg (operation of exchange of solvent by distillation). The distillation operation is repeated until the pyridine has been removed. When the temperature of the reactor is lowered to 20° C., 1000 ml of dichloromethane are added and the mixture is homogenized with stirring. 1000 ml of demineralized water and 100 ml of hydrochloric acid are successively introduced, the mixture is stirred for a further 30 minutes and, after separating by settling, the acidic aqueous phase is removed. These handling operations are repeated until a pH of the aqueous phase of approximately 1 is obtained. A solution composed of 1000 ml of demineralized water and 100 g of NaCl is introduced into the preceding mixture. The mixture is stirred for a further 30 minutes and allowed to separate by settling, and the aqueous phase is subsequently removed. These handling operations are repeated until a pH of the aqueous phase of 5.0 to 5.5 is obtained. The dichloromethane is subsequently removed by distillation at a temperature of 45° C. until a residual volume of 625 ml is obtained, and then the water is removed by four distillation operations at the same temperature with on each occasion 625 ml of dichloromethane.

The yield of stage 1 is 64%.

STAGE 2

Preparation of Compound C' (or 1,3,4-tri-O-acetyl-2,6-di-O-tosyl-glucose)

The concentrate obtained on conclusion of the preceding stage is taken up in 625 ml of dichloromethane (adjustment of the reaction volume to 1300 ml). The addition is carried out of 24 g of DMAP and then of 616 g of acetic anhydride in 1 h 30 min. at a temperature of 20° C. The reaction medium is heated to 43° C. and kept stirred for approximately 3 h. The degree of progression of the reaction is monitored by TLC (eluant: toluene/AcOEt 90/30 V/V). The reaction medium is cooled to 20° C. and 1000 ml of demineralized water are introduced. The reaction mixture is stirred for 30 min. and allowed to separate by settling, and the acidic aqueous phase is removed. 1000 ml of demineralized water and 100 g of $Na_2CO_3$ are subsequently added. Again, the reaction mixture is stirred for 30 min. and allowed to separate by settling, and the acidic aqueous phase is removed. Again, 1000 ml of demineralized water are added, followed by stirring for 30 min., separation by settling and removal of the aqueous phase. The organic phase is subsequently concentrated to a volume of between 875 ml and 1000 ml by removal of the dichloromethane by distillation under vacuum and then the dichloromethane is removed by distillation under vacuum with methanol, 500 ml of methanol being used on each occasion. The reaction volume is adjusted to 2000 ml by addition of methanol, the reaction medium is cooled with stirring to 0° C. and this temperature is maintained for 3 h. The precipitate obtained is filtered off. The cake obtained is subsequently washed three times by clarifying with 250 ml of methanol at 0° C. The product thus obtained (compound C') is dried under reduced pressure at 50° C. and to constant weight.

The yield of stage 2 is 95%, compound C' obtained exhibiting a purity of 93.4%, measured by HPLC assay.

STAGE 3

Preparation of Compound (I)

604 g of compound C' (0.98 mol) and 3600 ml of methanol are successively introduced into a 6 liter reactor. The mixture is stirred at a temperature of 20° C. 375.8 g of 30% sodium methoxide (MeONa)/methanol, i.e. 2.12 mol of methoxide, are subsequently added. The methanol used in this reaction stage is anhydrous (it comprises less than 200 ppm of water). The mixture is kept stirred at 20° C. for 5 h. The reaction medium is subsequently cooled to 0° C. and then the pH is adjusted to 6.5 by addition of 13.5 ml of hydrochloric acid (36%).

The cyclisation reaction of compound C' is selective and is reflected by a conversion of compound C' to compound (I) of at least 90%. Stages of washing and of removing solvents are subsequently necessary in order to obtain compound (I) in the isolated form.

The mixture is concentrated under reduced pressure at a temperature of 30° C. until a residual volume of 980 ml is obtained and then 1600 ml of ethyl acetate are added. The mixture is subsequently concentrated under reduced pressure at a temperature of 60° C. until a residual volume of 966 ml is obtained. 980 ml of ethyl acetate are introduced and the mixture is concentrated under reduced pressure at a temperature of 30° C. until a residual volume of 980 ml is obtained. 300 ml of ethyl acetate are again introduced and then the mixture is concentrated under reduced pressure at a temperature of 30° C. until a residual volume of 980 ml is obtained (operations to be repeated another two times still). The removal of the methanol is monitored by the refractive index of the final drops of distillate.

When all the methanol has been replaced by ethyl acetate, the reaction medium is cooled to 0° C. in 30 min. and is kept stirred at this temperature for 1 h. The suspension obtained is filtered and then the cake is washed by clarifying, four times and with, on each occasion, 300 ml of ethyl acetate, at 0° C. The filtration liquors thus obtained are combined. Concentrating is carried out under reduced pressure at a temperature of 25-30° C. until a residual volume of 780 ml is obtained.

The chemical yield of stage 3 is 75%.

The proton and carbon-13 NMR spectra of compound (I) are recorded on a Bruker 300 MHz device. The chemical shifts are expressed with respect to tetramethylsilane, to within 0.01 ppm for the proton spectrum and 0.1 ppm for the carbon-13 spectrum. The coupling constants are given as absolute value in Hz to within 0.5 Hz.

$^1$H NMR (CDCl$_3$): 2.67 (d, 1H, OH, J$_{4,OH}$ 5.5 Hz), 3.12 (d, 1H, H$_3$, J$_{2,3}$ 3.4 Hz), 3.42 (dd, 1H, H$_2$, J$_{2,3}$=J$_{2,1}$=3.0 Hz), 3.69 to 3.77 (m, 2H, H$_6$, H$_{6'}$), 3.89 (d, 1H, H$_4$, J$_{4,OH}$ 5.5 Hz), 4.40 (dm, 1H, H$_1$, J$_{1,2}$ 3.0 Hz).

$^{13}$C NMR: 49.3: C$_3$; 54.3: C$_2$, 65.6: C$_{6,6'}$; 67.1: C$_4$; 97.7: C$_1$; 74.2: C$_5$.

The invention claimed is:

1. A process for the preparation of compound (I):

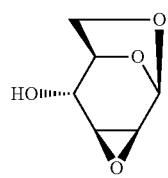

comprising a stage of cyclisation of compound C:

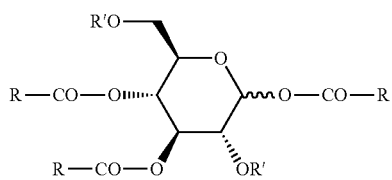

in which R represents an alkyl group comprising from 1 to 4 carbon atoms and R' represents an activating agent, in an alcohol/alkoxide mixture under anhydrous conditions.

2. The process according to claim 1, wherein in the compound C, R represents a methyl group.

3. The process according to claim 1 or claim 2, wherein in the compound C, R' represents a tosyl, mesyl or benzenesulphonyl group.

4. The process according to any one of claim 1 or 2 wherein the compound C corresponds to the formula C':

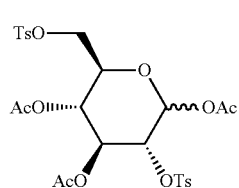

in which Ac represents an acetyl group and Ts represents a tosyl group.

5. The process according to any one of claim 1 or 2 wherein the cyclisation stage is carried out in a methanol/sodium methoxide mixture.

6. The process according to any one of claim 1 or 2 wherein the cyclisation stage is carried out using from two to three equivalents of alkoxide.

7. The process according to claim 1 further comprising:
a stage of acylation of compound B:

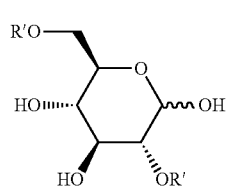

in which R' is as defined in claim 1, making it possible to obtain the compound C as defined in claim 1,
followed by the stage of cyclisation, as defined in claim 1, of compound C.

8. The process according to claim 7, wherein the compound B is such that R' represents a tosyl group and corresponds to the formula B':

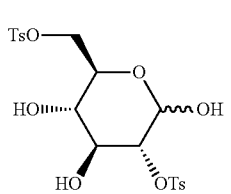

9. The process according to claim 7 or claim 8, characterized in that the acylation stage is an acetylation reaction.

10. The process according to claim 9, characterized in that the acetylation reaction is carried out using acetic anhydride.

11. The process according to claim 1 further comprising:
a stage of activation of compound A:

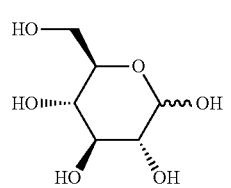

to obtain compound B:

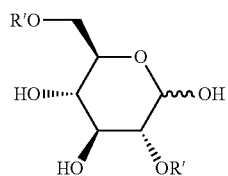

B

In which R' is as defined in claim 1
followed by a stage of acylation, of compound B, to obtain compound C as defined in claim 1,
followed by a stage of cyclisation, as defined in claim 1, of compound C.

12. The process according to claim 11, characterized in that the stage of activation of compound A is carried out using a tosyl, mesyl or benzenesulphonyl halide.

13. The process according to claim 7 further comprising:
a stage of activation of compound A:

A to obtain compound B as defined in claim 7,
followed by a stage of acylation, as defined in claim 7, of compound B, to obtain compound C:

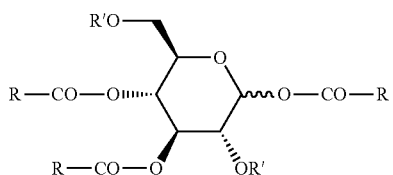

C followed by a stage of cyclisation of compound C to obtain compound (I):

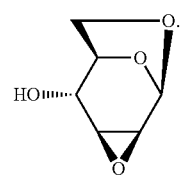

(I)

* * * * *